United States Patent [19]

East et al.

[11] Patent Number: 5,154,693
[45] Date of Patent: Oct. 13, 1992

[54] FLOW CONTROL DEVICE HAVING SELECTABLE ALTERNATIVE FLUID PATHWAYS

[75] Inventors: Gary P. East, Santa Barbara; David A. Watson, Goleta, both of Calif.

[73] Assignee: Pudenz-Schulte Medical Research Corp., Goleta, Calif.

[21] Appl. No.: 524,136

[22] Filed: May 15, 1990

[51] Int. Cl.⁵ ............................................. A61M 1/00
[52] U.S. Cl. ........................................ 604/9; 604/8; 604/153; 137/522
[58] Field of Search ..................................... 604/8-10, 604/247, 186; 137/522

[56] References Cited

U.S. PATENT DOCUMENTS

| | | |
|---|---|---|
| 4,552,553 | 11/1985 | Schulte et al. |
| 4,560,375 | 12/1985 | Schulte et al. ............................ 604/9 |
| 4,636,194 | 1/1987 | Schulte et al. |
| 4,741,730 | 5/1988 | Dormandy, Jr. et al. .............. 604/8 |
| 4,761,158 | 8/1988 | Schulte et al. ............................ 604/9 |
| 4,781,673 | 11/1988 | Watanabe ................................... 604/9 |
| 4,781,674 | 11/1988 | Redmond et al. ........................ 604/9 |
| 4,795,437 | 1/1989 | Schulte et al. ........................... 604/10 |
| 4,850,955 | 7/1989 | Newkirk .................................... 604/9 |
| 4,861,331 | 8/1989 | East et al. ................................. 604/9 |
| 4,867,741 | 9/1989 | Portnoy .................................... 604/10 |
| 4,995,864 | 2/1991 | Bartholomew et al. ................. 604/9 |

*Primary Examiner*—Robert A. Hafer
*Assistant Examiner*—Kerry Owens
*Attorney, Agent, or Firm*—Kelly, Bauersfeld & Lowry

[57] ABSTRACT

A flow control device for use in a subcutaneously implanted physiological shunt system includes a relatively rigid base and a resiliently flexible encasement which defines a fluid flow path therethrough from an inlet to an outlet. Two valves for controlling the flow of fluid through the device are situated serially within the fluid flow path between the inlet and the outlet. The fluid flow path includes a first fluid conduit which directs fluid through both valves, and a second fluid conduit which bypasses the first valve and directs fluid only through the second valve. The first valve is constructed to provide a greater resistance to flow through the device than the second valve, and when the second fluid conduit is unobstructed, fluid will tend to flow through the second fluid conduit and bypass the first valve. A plug is integrally formed with a portion of the encasement, for occluding the second fluid conduit. The plug can be inserted into a receiving collar to occlude the second fluid conduit, by manual percutaneous pressure, thereby requiring all fluid flow through the device to pass through the first fluid conduit. A siphon control device is provided between the valves and the outlet to prevent fluid flow in the absence of positive upstream fluid pressure or in response to negative downstream hydrostatic pressure on the outlet of the device.

34 Claims, 4 Drawing Sheets

FLOW CONTROL DEVICE HAVING SELECTABLE ALTERNATIVE FLUID PATHWAYS

BACKGROUND OF THE INVENTION

This invention relates generally to surgically implanted physiological shunt systems and related flow control devices. More particularly, the present invention relates to shunt systems including one-way flow control valves for controlling the flow of cerebrospinal fluid out of a brain ventricle and preventing backflow of fluid into the brain ventricle.

In the medical arts, to relieve undesirable accumulation of fluids it is frequently necessary to provide a means for draining a fluid from one part of the human body to another in a controlled manner. This is required, for example, in the treatment of hydrocephalus, a ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube which conducts the fluid away from the brain to be reintroduced into the peritoneal cavity or into the vascular system, as by extending a distal catheter through the patient's jugular vein to the atrium portion of the heart. To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of over drainage of the cerebrospinal fluid from the brain ventricles sometimes exists. Over drainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter. This over drainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such over drainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

It is desirable in some instances to permit the physician to be able to alter the flow characteristics through the drainage system after it has been subcutaneously implanted. To this end, on-off devices have been provided for implantation as a portion of the fluid conduit, as an additional element of the shunt. An exemplary on-off device is shown in U.S. Pat. No. 3,827,439.

Prior physiological shunt systems have failed to provide, however, a flow control device which permits only unidirectional flow through the shunt system, prevents over drainage caused by the siphoning effect of hydrostatic pressure in the distal shunt catheter, and permits the flow characteristics through the shunt to be altered by means of percutaneous pressure after the shunt system has been surgically implanted. Further, existing flow control devices extensively used in connection with the treatment of hydrocephalus typically provide only a single pre-set resistance to the flow of excess cerebrospinal fluid through the shunt system, which cannot be varied except to prevent fluid flow through the shunt by means of an on-off valve.

Accordingly, there has been a continuing need in the medical arts for convenient and effective physiological drainage devices for controlling the flow of fluid from one part of the body to another, which are relatively inexpensive to manufacture and can be constructed substantially of non-metallic parts which are not subject to adhering to one another and causing a malfunction of the device. A flow control device is needed which permits fluid flow therethrough only when upstream fluid pressure exceeds downstream fluid pressure by a selected pressure differential, and which also provides means for altering the selected pressure differential by manual percutaneous manipulation of the device when it is subcutaneously implanted.

Additionally, a novel flow control device for use in a physiological shunt system is needed which utilizes a plurality of flow control valves having different flow control characteristics. Such a device should provide alternative fluid pathways therethrough such that selection of the desired fluid pathway can be made by the selective application of percutaneous manual pressure to the device when it is subcutaneously implanted. Moreover, such a flow control device is needed which incorporates an integral siphon control device that opens only in response to positive upstream fluid pressure, and recloses or remains closed in the absence of such positive upstream fluid pressure or in response to negative downstream hydrostatic pressure on the device. As will become apparent from the following description, the present invention satisfies these needs and provides other related advantages.

SUMMARY OF THE INVENTION

The present invention resides in a physiological shunt system for controlling the flow of fluid from one part of the body to another, which is constructed substantially of non-metallic materials and provides trouble-free and reliable operation in use. The shunt system of the present invention is relatively inexpensive to manufacture, and can be easily modified to provide a variety of pressure/flow characteristics. In accordance with the present invention, a flow control device for use in a subcutaneously implanted physiological shunt system includes a housing having an inlet and an outlet, a fluid flow path through the housing from the inlet to the outlet, and means for controlling fluid flow through the fluid flow path. The controlling means includes means for permitting fluid flow through the fluid flow path when upstream fluid pressure exceeds downstream fluid pressure by a selected pressure differential, and means for altering the selected pressure differential by manual percutaneous manipulation of the flow control device when it is subcutaneously implanted.

In a preferred form of the invention, the controlling means includes a first normally closed valve which opens to permit fluid flow through the fluid flow path when upstream fluid pressure exceeds downstream fluid pressure by a first pressure differential, and a second normally closed valve which opens to permit fluid flow through the fluid flow path when upstream fluid pressure exceeds downstream fluid pressure by a second pressure differential. Preferably, the first pressure differential is greater than the second pressure differential.

The fluid flow path includes a first fluid conduit for directing fluid through the first and second normally closed valves, and a second fluid conduit which bypasses the first normally closed valve and directs fluid through the second normally closed valve only. The means for altering the selected pressure differential comprises means for selectively directing fluid either through the first or second fluid conduits.

The first and second normally closed valves each include a base having a valve passageway therethrough, and a valve seat surrounding a portion of the valve passageway. A flow control member is attached to each base so as to contact the valve seat in a manner normally occluding the valve passageway, but selectively opening to permit controlled unidirectional flow therethrough. Each flow control member includes a central support and a resilient membrane. The central support is attached to the base and extends therefrom to support the resilient membrane. The resilient membrane is generally arch-shaped and has a portion thereof capable of engaging the valve seat to occlude the valve passageway.

A variety of pressure/flow characteristics can be provided by the flow control device of the present invention by manufacturing the normally closed valves with different resilient membranes of varying thicknesses. The resistance to flow past a normally closed valve increases with an increase in membrane thickness.

The means for selectively directing fluid either through the first or second fluid conduits includes means for occluding the second fluid conduit means. This occluding means includes a plug insertable into the second fluid conduit by manual percutaneous pressure applied to the device. The plug is retained within a collar to occlude the second fluid conduit and thus require all fluid flow through the device to pass through the first fluid conduit. The plug can be dislodged from the collar to open the second fluid conduit by additional selective manual percutaneous manipulation of the device.

In order to provide the desired resistance to adhesion between various components of the flow control device, particularly during storage, rigid components of the valve are generally formed of a rigid polypropylene material, while elastic components, such as the valve resilient membranes, are preferably molded of a silicone elastomer material.

An intermediate fluid passageway between the inlet and the normally closed valves is configured to provide a flushing reservoir, and integral flow occluders are provided generally adjacent to the inlet and the outlet, all of which are operated by percutaneous finger pressure applied to the device. Through selective application of percutaneous pressure to the flow occluders and the flushing reservoir, fluid within the reservoir can be selectively flushed both proximally and distally through the device.

A siphon control device is situated between the normally closed valves and the outlet, to prevent fluid flow through the flow control device in the absence of positive upstream fluid pressure or in response to negative downstream hydrostatic pressure. The siphon control device comprises an integral housing including a pair of spaced, substantially parallel, flexible diaphragms, and a base invested within the housing. The base and housing define a fluid flow pathway between the normally closed valves and the outlet.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

As shown in the drawings for purposes of illustration, the present invention is concerned with an improved flow control device, generally designated in the accompanying drawings by reference number 10. The improved flow control device 10 is intended for use in a surgically implanted physiological shunt system for draining fluid from one portion of the body to another. In order to connect, for example, the device 10 in such a system, the device includes an inlet connector 12 and an outlet connector 14 which each receive one end of a piece of surgical tubing (not shown). The ends of the surgical tubing are placed over the connectors 12 and 14 and secured thereon by a single ligature just inside of an annular ridge 16 formed near the end of each connector.

When the flow control device 10 is used in a drainage system intended for the treatment of hydrocephalus, the inlet connector 12 is fluidly connected with a proximal catheter which is inserted through the skull into a brain ventricle containing cerebrospinal fluid under pressure. The outlet connector 14 is fluidly connected to a distal catheter which serves to discharge cerebrospinal fluid into, for example, the atrium portion of a patient's heart.

Ordinarily the flow control device 10 will be surgically implanted on the patient's skull with a flap of skin overlying the device. To facilitate holding the device in its desired position after implantation, a generally flexible mounting plate 18 can be provided with one or more suture holes.

As will become apparent from the following description, the present invention provides a highly reliable flow control device having selectable alternative fluid pathways which permit the flow control characteristics of the device 10 to be altered when subcutaneously implanted by manual percutaneous manipulation of the device. The present invention provides a highly reliable flow control device designed to prevent valve seat deformation and membrane to valve seat sticking, and to facilitate implantation by eliminating components to be connected or adjusted other than the surgical tubing to the device itself.

In accordance with the present invention, the flow control device 10 includes a pair of relatively rigid, molded plastic bases 20 and 22 invested within a resiliently flexible housing 24 which, together, define a fluid flow path through the housing from the inlet connector 12 to the outlet connector 14. Two normally closed valves 26 and 28 are provided within the fluid flow path to restrict the flow of fluid through the device 10. The housing 24 and the second base 22 cooperate to provide a siphon control device 30, situated between the valves 26 and 28 and the outlet connector 14, which prevents fluid flow through the device 10 in the absence of positive upstream fluid pressure or in response to negative downstream hydrostatic pressure on the device. Further, the housing 24 and the first base 20 cooperate to define a pump or flushing reservoir 32 between the inlet connector 12 and the valves 26 and 28.

Two alternative fluid conduits, defining portions of the fluid flow path through the device 10, are provided in order to permit the flow control characteristics of the device 10 to be altered by manual percutaneous pressure applied to the device when subcutaneously implanted. A first fluid conduit 34 directs fluid through both the first and second normally closed valves 26 and 28. A second fluid conduit 36 bypasses the first normally closed valve 26 and directs fluid through the second normally closed valve 28 only.

More specifically, and as shown best in FIGS. 2-7, the bases 20 and 22 interfit with one another and are integrally formed with, respectively, the inlet and outlet connectors 12 and 14. The first base 20 is integrally formed with the inlet connector 12 and defines an inlet flow channel 38 extending the inlet connector 12 to an upwardly facing inlet occluder port 40. The first base 20 further forms a bottom plate 42 for the flushing reservoir 32, and a generally cylindrical receptacle 44 which receives a portion of the second base 22.

The second base 22 is integrally formed with the outlet connector 14 and includes a generally cylindrical valve housing 46 which is received, in an interference fit, into the receptacle 44 of the first base 20. The valve housing 46 includes a housing key 48 which snap-fits into an aperture provided through the receptacle 44, for the purpose of properly aligning the second base 22 with respect to the first base 20. The second base 22 defines a valve housing outlet flow channel 50 which terminates at an upwardly facing outlet occluder port 52. Between the outlet occluder port 52 and the outlet connector 14, the second base 22 defines a portion of the siphon control device 30.

The flexible housing 24 is provided in two parts: an inlet housing portion 24a in which the first base 20 and a portion of the second base 22 are invested, and an outlet housing portion 24b which is sealed by a suitable adhesive 54 to the inlet housing portion 24a in order to provide a continuous elastomeric exterior to the device 10, with the exception of the inlet and outlet connectors 12 and 14 which extend therefrom. The inlet housing portion 24a is integrally formed with the mounting plate 18 and includes an inlet aperture through which the inlet connector 12 extends, an inlet occluder wing 56 which generally overlies the inlet occluder port 40, and a resiliently flexible dome 58 for the flushing reservoir 32. The inlet housing 24a surrounds the receptacle 44 and adjacent portions of the second base 22, and includes a recess 60 in which an engaging flange 62 of the outlet housing 24b is secured by means of the adhesive 54.

In order to provide a fluid-tight seal between the inlet connector 12 and the housing 24a, a tube 64 is placed over a portion of the inlet connector and secured in place by means of an over suture 66. A silicone adhesive 68 is then injected into the remaining gap between the housing 24a and the inlet connector 12. This same sealing arrangement is made between the housing 24b and the outlet connector 14.

The inlet occluder wing 56 is positioned over the inlet occluder port 40 to facilitate occluding the inlet flow channel 38 at the port 40 by pressing the wing 56 downwardly. Depressing the wing 56 and occluding the port 40 prevents proximal fluid flow from the flushing reservoir 32, defined by the dome 58 and the bottom plate 42, when the dome is pressed downwardly by manual percutaneous pressure (see FIG. 5). The dome 58 is preferably molded of a silicone elastomer material and is designed to permit injection into the flow control device 10 by a hypodermic needle through the dome. The bases 20 and 22 are preferably molded of a polypropylene material which provides sufficient rigidity to prevent a needle from inadvertently passing through the device 10 if an injection is made into the flushing reservoir 32. The construction of the bases 20 and 22 and the housing 24 helps to guide a physician in manually percutaneously manipulating the device 10 when subcutaneously implanted, for purposes of flushing the shunt system and/or altering the flow characteristics of the flow control device.

The outlet housing portion 24b surrounds a portion of the second base 22 to define the siphon control device 30 which is similar to that shown and described in U.S. Pat. No. 4,795,437, the contents of which are incorporated herein by reference. The siphon control device 30 includes an outer wall 70 and an inner wall 72 which is situated within and encircled about by the outer wall. The valve housing outlet flow channel 50 channels fluid from the second normally closed valve 28 to a central SCD reservoir 74 defined as the area between the inner wall 72 and the outer wall 70. An outlet flow channel 76 extends through the inner wall 72 to the distal end of the outlet connector 14.

Figure 1:
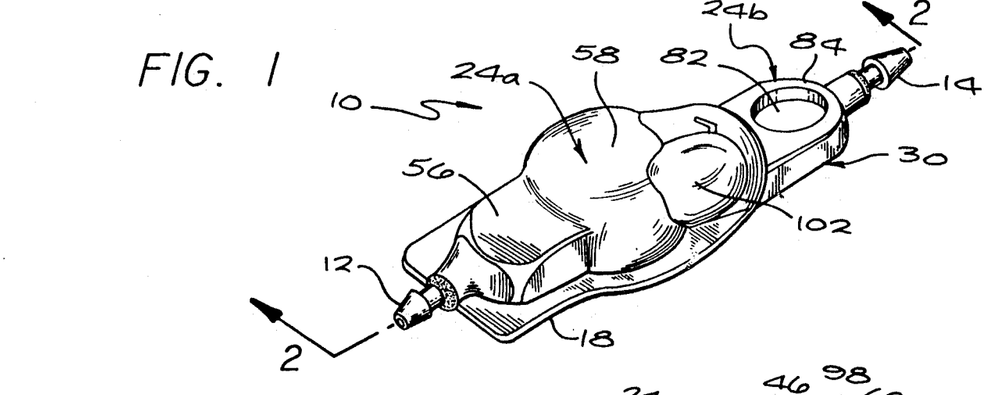
FIG. 1 is a perspective view of a flow control device having selectable alternative fluid pathways, embodying the invention.
Figure 2:
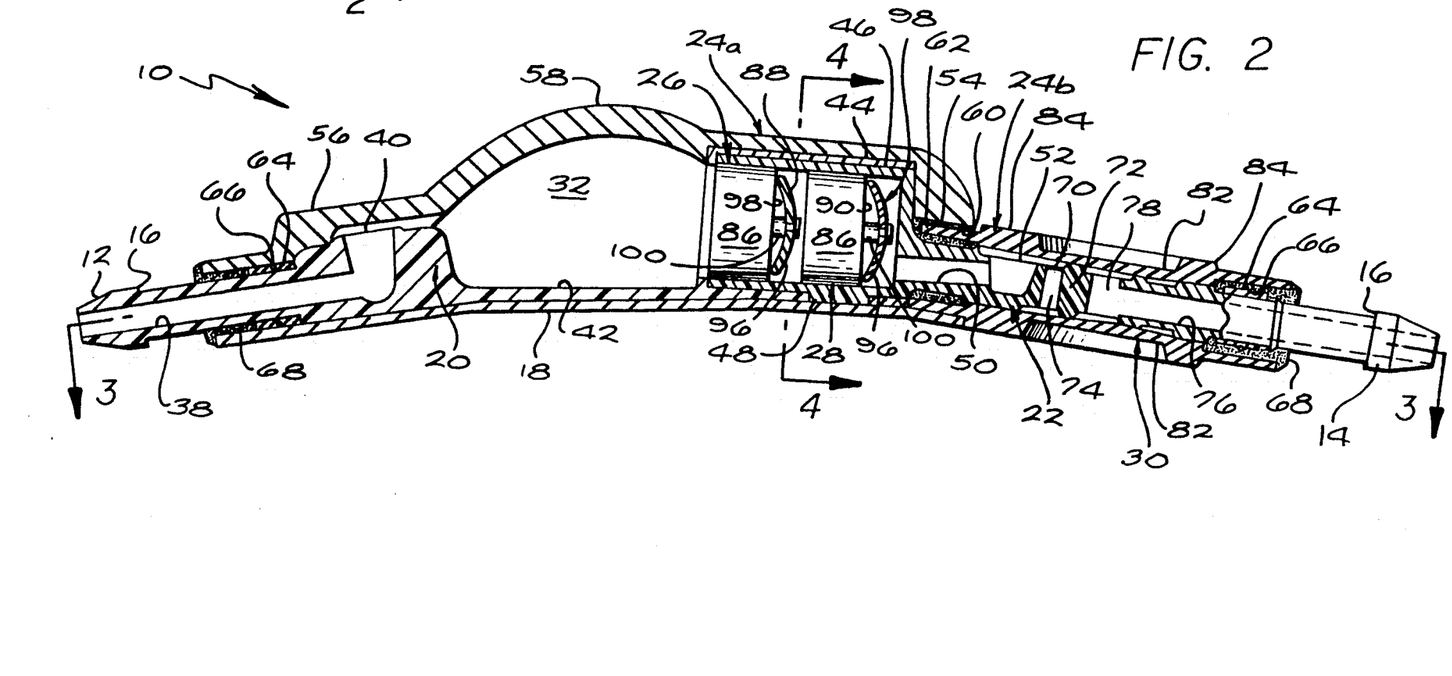
FIG. 2 is an enlarged vertical section taken generally along the line 2—2 of FIG. 1.
Figure 3:
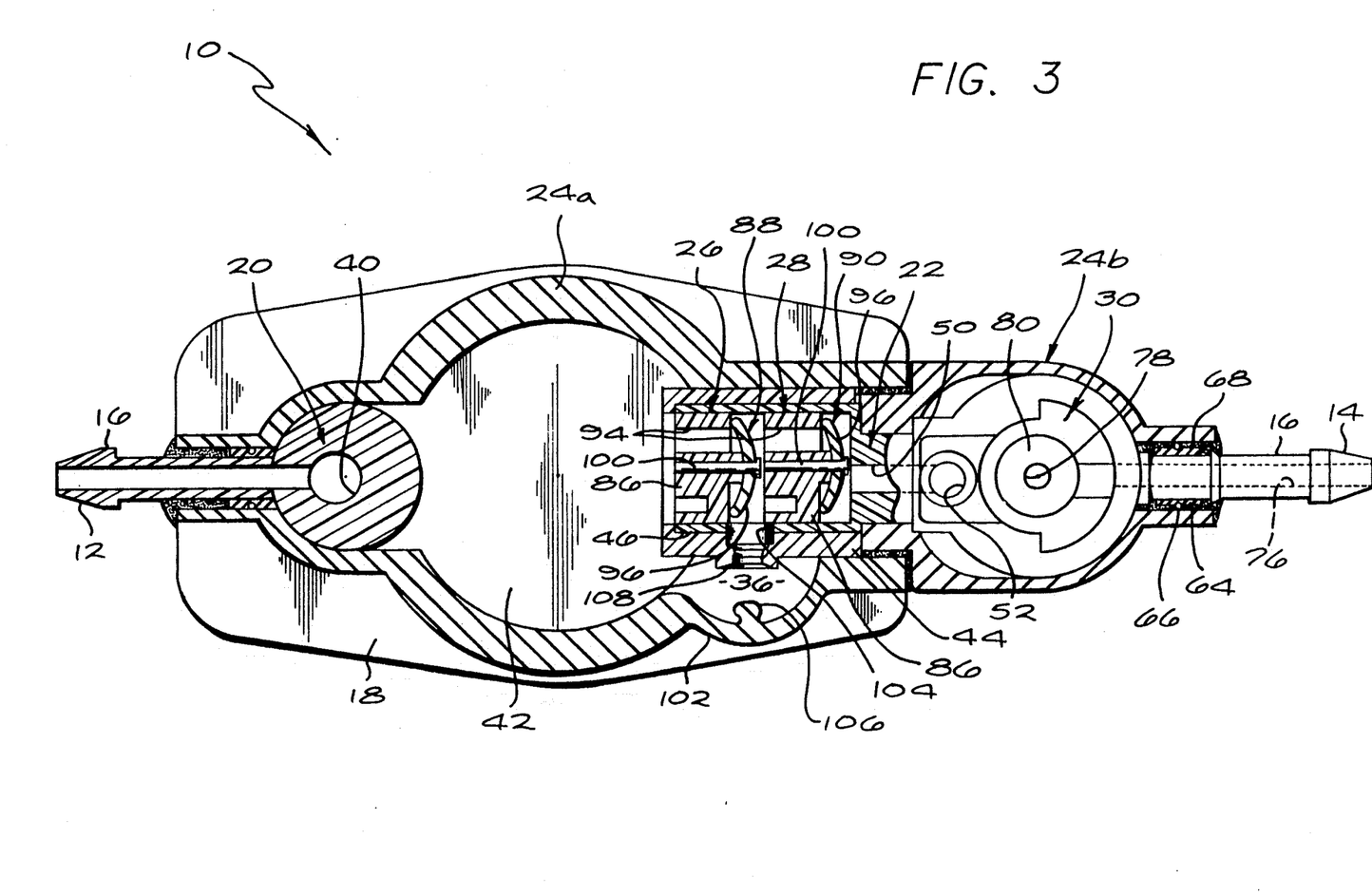
FIG. 3 is a horizontal section taken taken generally along the line 3—3 of FIG. 2, illustrating the configuration of the flow control device when the second fluid conduit is open to fluid flow.
Figure 4:
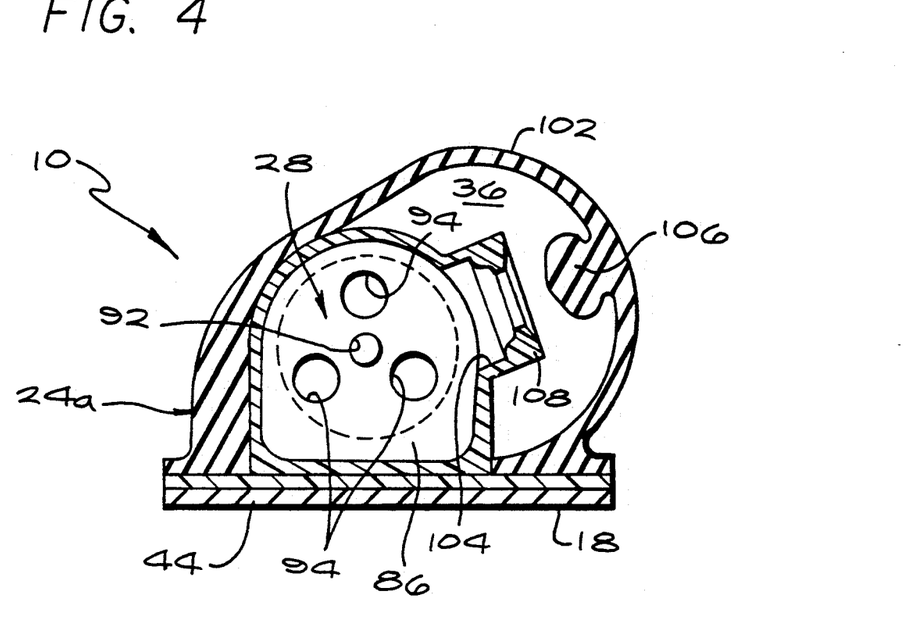
FIG. 4 is an enlarged vertical section taken generally along the line 4—4 of FIG. 2, illustrating the configuration of a plug which is positioned so as not to occlude the second fluid conduit.

As can be seen best in FIG. 3, the outer wall 70 is generally circular in shape, and is spaced from and encircles the inner wall 72. The inner wall is also generally circular in shape, and defines an outlet chamber 78 which is adjacent to and in fluid communication with the outlet flow channel 76. The inner wall 72 is constructed to have substantially parallel upper and lower seating surfaces 80, and it effectively forms a barrier separating the SCD reservoir 74 from the outlet chamber 78.

The outlet housing portion 24b is provided with a pair of spaced, substantially parallel, flexible and elastic diaphragms 82 which are fixed about their peripheries adjacent to the outer wall 70. Each diaphragm has an inner surface which defines the upper and lower limits of the SCD reservoir 74 and the outlet chamber 78, and an outer surface which forms an exterior surface of the siphon control device 30. The diaphragms 82 are situated on opposite sides of the inner wall 72 to position a portion of each inner surface thereof in contact with an adjacent one of the seating surfaces 80 and form a seal therebetween which prevents fluid flow between the outlet occluder port 52 and the outlet flow channel 76.

The outlet housing portion 24b further includes integral offset rings 84 which surround each diaphragm 82 to inhibit overlying tissue from occluding the siphon control device 30 when implanted into a patient. An aperture is provided through the housing 24b through which the outlet connector 14 extends. A fluid tight seal is effected between the housing outlet aperture and the outlet connector 14 utilizing a tube 64, an over suture 66 and an adhesive 68, as described above in connection with the inlet housing portion 24a and the inlet connector 12.

In use, the diaphragms 82 normally lie against and interact with the seating surfaces 80 of the inner wall 72 to close the device 10 to fluid flow. The diaphragms 82 move away from the seating surfaces 80, however, in response to a minimal level of positive fluid pressure within the SCD reservoir 74 to permit passage of fluid from tee valve housing flow channel 50 to the outlet flow channel 76 (see FIG. 5). The diaphragms 82 close and seal upon the seating surfaces 80 once again in the absence of such positive upstream fluid pressure, or in response to negative downstream hydrostatic pressure in the outlet chamber 78. The siphon control device 30 thus minimizes the undesirable consequences attendant to excessive over drainage of fluid due to the siphoning effect of hydrostatic pressure.

With reference now to the normally closed valves 26 and 28, each valve includes a valve membrane carrier 86 which is securely positioned within the valve housing 46 of the second base 22. Each valve membrane carrier 86 provides a cylindrical support for a respective flow control member 88 or 90, and is press-fit within the valve housing 46.

Each of the valve membrane carriers 86 includes a cylindrical outer portion which abuts against a correspondingly shaped inner surface of the valve housing 46 to form a fluid tight seal therebetween. A central reinforced aperture 92 is provided for receiving a portion of the respective flow control member 88 or 90, and the central aperture 92 is surrounded by three additional apertures 94 which provide a plurality of channels through which fluid is permitted to flow.

The valves 26 and 28 are arranged serially within the valve housing 46 for controlling the flow of cerebrospinal fluid out of a brain ventricle. Each flow control member 88 and 90 includes a membrane 96, molded of a synthetic polymer material different from the material of the valve membrane carrier 86, which is secured relative to the valve membrane carriers to generally cover the apertures 94.

The resilient membranes 96 are normally biased to close communication between inlet and outlet sides of each valve 26 and 28, but will open to permit flow when the pressure on the inlet or proximal side of the resilient membrane exceeds the pressure on the outlet or distal side by a predetermined amount. Moreover, should the pressure on the distal side of either resilient membrane 96 ever exceed the pressure on the proximal side, tending to cause flow in a reverse direction through the valves 26 and 28, the membrane 96 will seal tightly against a valve seat 98 provided on the valve membrane carrier 86, to prevent any such reverse fluid flow.

The valve membrane carriers 86 are preferably formed of a polypropylene material, and the membranes 96 are preferably formed of a silicone elastomer material. Both polypropylene and elastomer materials have been shown to produce an acceptable level of tissue reaction, and the use of this particular duality of materials, in contrast to the use of only a single material, markedly decreases the chance of the membranes 96 adhering to any portion of the valve membrane carriers 86, which would clog the drain passage and defeat the purpose of the valves 26 and 28.

An added advantage of using these particular materials is the avoidance of the negative effect of metal components, due to radiation scatter or "sunburst effect," on films taken by, for example, computerized axial tomography (CAT) scanning equipment. This type of scanning frequently accompanies the use of surgically implanted flow control valves, and the absence or limitation of metal in the areas scanned will permit more accurate and complete results to be gathered from CAT scanning.

The flow control members 88 and 90 each include a rigid nail 100 having an elongated shaft and an expanded head at an end of the shaft. The nail 100 is capable of being driven into the central aperture 92 of the respective valve membrane carrier 86 to be frictionally retained therein. The nail 100 is preferably constructed of a polypropylene material which will not stretch or flex as the nail is being driven into the central aperture 92. After the nail is properly placed within the aperture, it is preferably heat welded in place.

The membranes 96 have an arch-shape, as for example a section of a sphere, and are designed to contact the valve seats 98 generally along the outer edges of the membrane in a manner surrounding the apertures 94. Each membrane 96 is secured to its respective valve membrane carrier 86 by the central support/nail 100. The membrane is retained in place on the nail by an interference fit or by use of an adhesive, or by any other suitable means.

Since the valves 26 and 28 are primarily designed to provide controlled resistance to cerebrospinal fluid flow from a brain ventricle to another location in the body, it will be appreciated that a doctor must be able to select valves having the particular pressure/flow characteristics desired for each individual application. That is, a valve which permits flow at a relatively low pressure differential may not be suitable where the maintenance of a higher pressure differential is indicated. Toward this end, in order to provide a flow control device with a variety of different pressure/flow characteristics, the first normally closed valve 26 has a different pressure/flow characteristic than the second normally closed valve 28. More particularly, the first normally closed valve 26 is provided with a relatively thick membrane 96, whereas the second normally closed valve 28 is provided a relatively thin membrane 96. Resistance to flow increases with an increase in membrane thickness. Thus, the first normally closed valve provides a higher degree of resistance to flow through the device 10 than the second normally closed valve 28.

Recognizing that fluid will tend to take the path of least resistance, it can be seen that fluid permitted to flow through the second fluid conduit 36, thereby bypassing the first normally closed valve 26, will experience a lesser degree of resistance to flow than if forced to flow through the first fluid conduit 34. FIGS. 1 through 4 illustrate the configuration of the flow control device 10 wherein the second fluid conduit 36 is open to fluid flow therethrough. The inlet housing portion 24a includes a bypass portion 102 which overlies aligned apertures 104 provided through both the receptacle 44 and the valve housing 46. As shown best in FIGS. 3 and 4, fluid is permitted to flow from the flushing reservoir 32 between the bypass portion 102 and the first base 20, and through the aligned apertures 104 for introduction on the inlet side of the second normally closed valve 28. Since both of the normally closed valves 26 and 28 prevent retrograde fluid flow, the fluid passes only through the second normally closed valve 28 into the valve housing outlet flow channel 50. Accordingly, resistance to flow through the flow control device 10 when the second fluid conduit 36 is open, is determined primarily by the second normally closed valve 28. From the flow channel 50, the fluid then passes through the siphon control device 30 to the outlet flow channel 76, for delivery to a distal catheter.

Integrally formed with the bypass portion 102 is a plug 106 configured to occlude the aligned apertures 104. The receptacle 44 includes a collar 108 designed to retain the plug 106 therein (FIGS. 6 and 7) when inserted by manual percutaneous pressure applied to the bypass portion 102 of the housing 24a. With the plug 106 held in place by the collar 108 to occlude the aligned apertures 104, fluid flow through the second fluid conduit 36 is prevented, thereby requiring any fluid flow through the flow control device 10 to occur solely through the first fluid conduit 34.

Figures 5, 7:
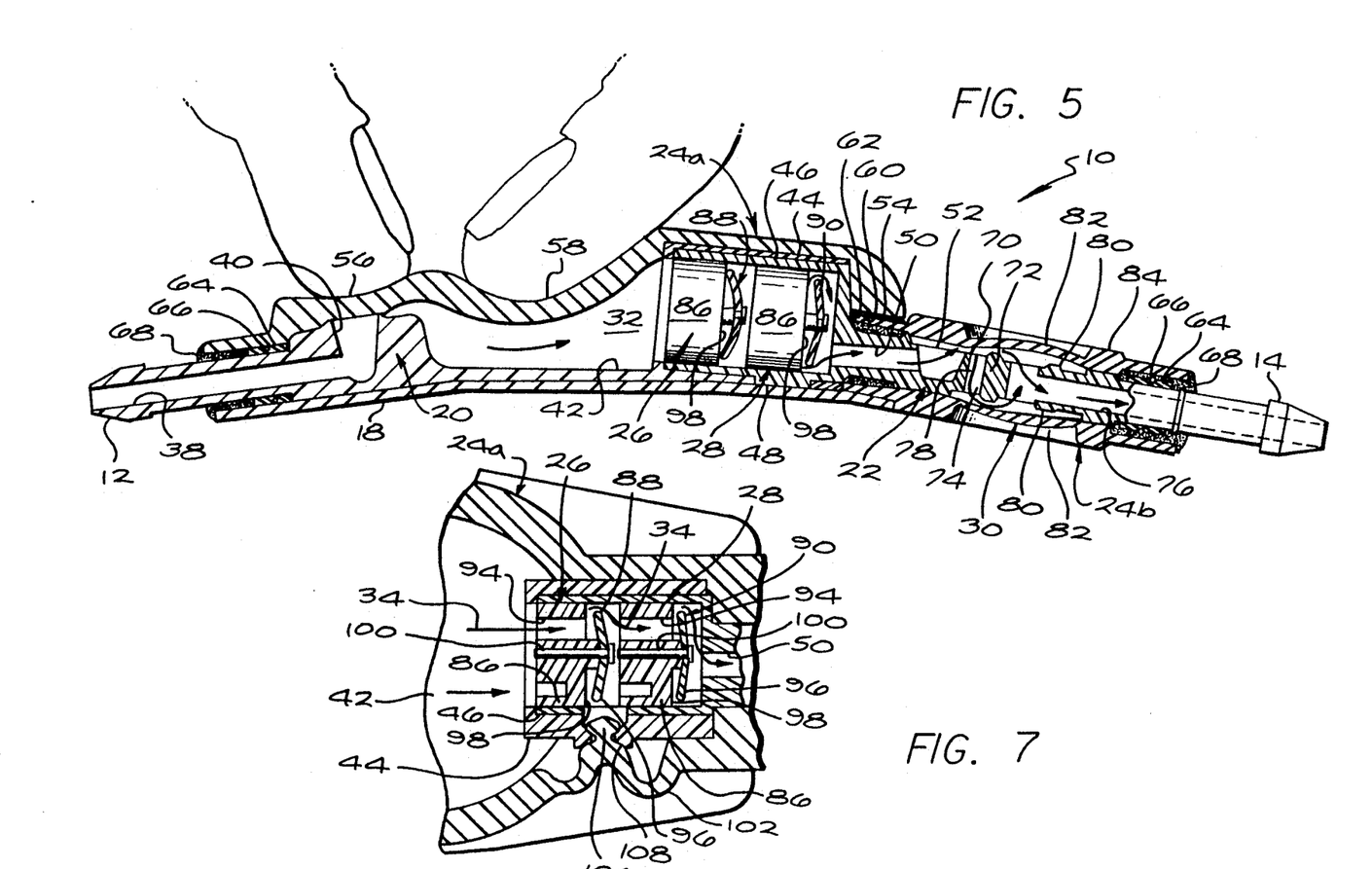
FIG. 5 is a vertical sectional view similar to that illustrated in FIG. 2, illustrating the manner in which a portion of the fluid flow path adjacent to an inlet can be occluded by manual percutaneous pressure, and the manner in which additional manual percutaneous pressure can be applied to a portion of the housing to flush fluid through the device.
FIG. 7 is a horizontal sectional view similar to FIG. 3, illustrating, in fragmented form, a portion of the flow control device and the manner in which fluid flows past two normally closed valves when the second fluid conduit is occluded.
Figure 6:
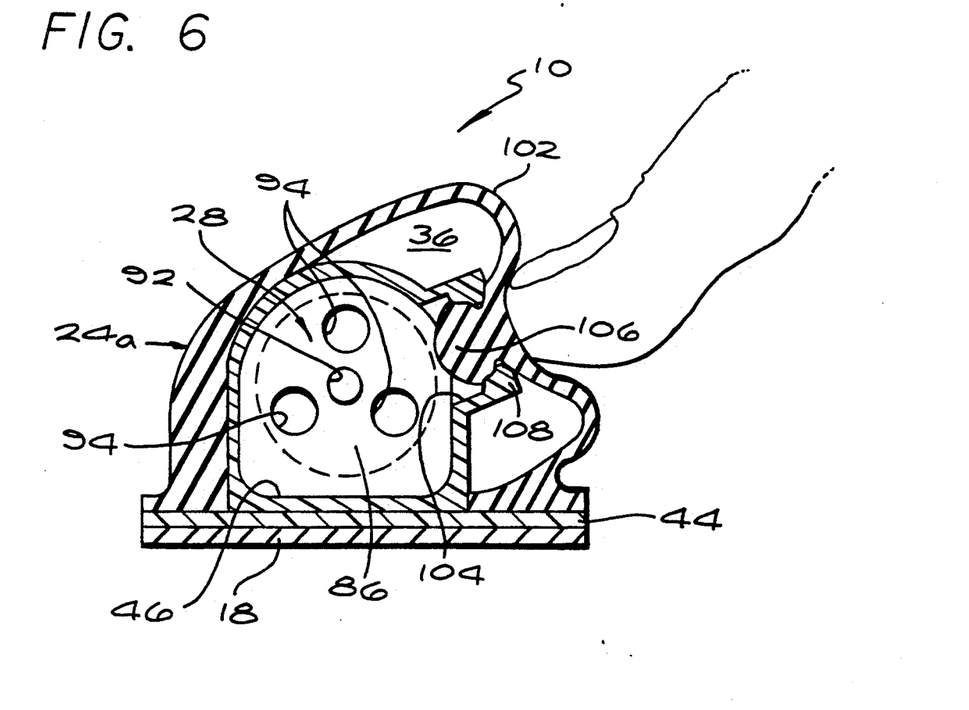
FIG. 6 is a vertical sectional view similar to FIG. 4, illustrating the manner in which the plug can be inserted into a collar defining a portion of the second fluid conduit, to occlude the second fluid conduit to fluid flow therethrough.

Fluid flow through the first fluid conduit 34 is illustrated best in FIG. 7, which shows that fluid within the flushing reservoir 32 must pass through both the first and second normally closed valves 26 and 28. Since the first normally closed valve 26 provides a greater degree of resistance to flow than the second normally closed valve 28, the first valve 26 primarily determines the resistance to flow of the device 10 in this configuration.

The design of the flow control device 10, as described above, lends itself to easy percutaneous distal and proximal flushing, and permits the selective adjustment of flow characteristics by percutaneous manual manipulation when subcutaneously implanted. In order to flush the device 10 distally, the inlet occluder wing 56 is pressed downwardly to occlude the inlet occluder port 40. The dome 58 is then simply pressed downwardly (FIG. 5) to flush the contents of the flushing reservoir 32 through the second fluid conduit 36 (or the first fluid conduit 34 if the second fluid conduit is occluded), past the siphon control device 30 and through the outlet flow channel 76. Similarly, proximal flushing can be accomplished by pressing downwardly the offset ring 84 of the siphon control device 30 adjacent to the distal end of the inlet housing portion 24a, to occlude the outlet occluder port 52. The dome 58 is then pressed downwardly to flush fluid proximally from the flushing reservoir 32 out of the device 10 through the inlet flow channel 38.

In order to dislodge the plug 106 from the collar 108 and thereby open the second fluid conduit 36, pressure is applied to the housing 24 to occlude both the inlet occluder port 40 and the outlet occluder port 52, and then the dome 58 is depressed as if to flush the device 10. However, since both the distal and proximal flow paths for fluid within the flushing reservoir 32 are occluded, the static fluid pressure between the occluder ports 40 and 52 is raised sufficiently to dislodge the plug 106 from the collar 108. The housing 24 is preferably formed of a resiliently flexible material so that after dislodging the plug 106 from the collar 108, the bypass portion 102 of the housing takes on its original shape to permit fluid flow through the aligned apertures 104 of the second fluid conduit 36.

From the foregoing it is to be appreciated that the present invention provides a flow control device 10 for use in a subcutaneously implanted physiological shunt system having selectable alternative means for controlling fluid flow through the fluid flow path. Through the provision of a first fluid conduit 34 which directs fluid through both the first and second normally closed valves 26 and 28, and an alternative second fluid conduit 36 which bypasses the first normally closed valve 26, means are provided for permitting fluid flow when upstream fluid pressure exceeds downstream fluid pressure by two different selected pressure differentials. The construction of the flow control device 10 of the present invention permits selective distal and proximal flushing of the device through the application of manual percutaneous pressure, and further permits the selected pressure differential to be altered, also through percutaneous manual manipulation of the device when subcutaneously implanted. The present invention provides a device by which the flow of cerebrospinal fluid out of a brain ventricle can be controlled while preventing the backflow of fluid into the brain ventricle, and inhibits excessive drainage through the physiological shunt in the presence of excessive downstream suction.

Although a particular embodiment of the invention has been described in detail for purposes of illustration, various modifications may be made without departing from the spirit and scope of the invention. Accordingly, the invention is not to be limited, except as by the appended claims.

We claim:

1. A fluid control device, comprising:
   an inlet;
   an outlet;
   a first fluid flow pathway between the inlet and the outlet;
   a second fluid flow pathway between the inlet and the outlet;
   at least two valves for restricting the flow of fluid through the device, the valves being situated serially within the first fluid flow pathway between the inlet and the outlet; and
   means for selectively directing fluids through one of the first or the second fluid flow pathways, wherein the first fluid flow pathway directs fluid through the at least two valves, and the second fluid flow pathway bypasses at least one of the valves and directs fluid through at least another one of the valves.

2. A fluid flow control device as set forth in claim 1, wherein the at least two valves include a first valve and a second valve situated in the first fluid flow pathway between the first valve and the outlet, the first valve providing a greater resistance to flow than the second valve.

3. A fluid flow control device as set forth in claim 2, wherein the first and second valves each include a base having a fluid passageway therethrough and a valve seat surrounding a portion of the fluid passageway, and a flow control member attached to the base and contacting the valve seat in a manner normally occluding the fluid passageway but selectively opening to permit controlled undirectional flow therethrough.

4. A fluid flow control device as set forth in claim 3, wherein each flow control member includes a central support and a resilient membrane, the central support comprising a rigid nail and being attached to the respective base and extending therefrom to support the resilient membrane, the resilient membrane being generally arch-shaped and having a portion thereof capable of engaging the respective valve seat to occlude the respective fluid passageway.

5. A fluid flow control device as set forth in claim 1, wherein the means for selectively directing fluids through one of the first or the second fluid flow pathways includes means for occluding the second fluid flow pathway.

6. A fluid flow control device as set forth in claim 5, wherein the means for occluding the second fluid flow pathway includes plug means insertable into the second fluid flow pathway by manual percutaneous pressure applied to the device, which plug means is retained in place to occlude the second fluid flow pathway in the absence of a dislodging percutaneous manipulation of the device.

7. A fluid flow control device as set forth in claim 1, including an intermediate fluid passageway between the inlet and the at least two valves, and means for flushing fluids from the intermediate fluid passageway by application of percutaneous manual pressure to the device.

8. A fluid flow control device as set forth in claim 7, including means for temporarily occluding a portion of the first fluid flow pathway adjacent to the inlet by application of percutaneous manual pressure to the device, and means for temporarily occluding a portion of the first fluid flow pathway adjacent to the outlet by application of percutaneous manual pressure to the device.

9. A fluid flow control device as set forth in claim 1, including a siphon control device situated adjacent to the outlet and forming a portion of the first fluid flow pathway, the siphon control device comprising:
- an integral housing including a pair of spaced, substantially parallel flexible diaphragms having inner and outer surfaces, and top and bottom integral rings wherein each is positioned to surround a respective diaphragm to provide means for inhibiting overlying tissue from occluding the device; and
- a base invested within the housing, the base including a wall having an inlet side and an outlet side, and substantially parallel upper and lower seating surfaces;
- wherein the base and housing define a portion of the first fluid flow pathway adjacent to the outlet, the diaphragms being situated on opposite sides of the wall to position a portion of each inner surface to be normally in contact with an adjacent one f the seating surfaces and form a seal therebetween which prevents fluid flow between the inlet side and the outlet side of the wall, wherein the diaphragms will move away from the seating surfaces in response to positive fluid pressure on the inlet side of the wall to permit passage of fluid through the device, but will form a seal with the seating surfaces to prevent such fluid flow in the absence of such positive fluid pressure or in response to negative hydrostatic pressure on the outlet side of the wall.

10. A fluid flow control device, comprising:
- a housing having an inlet and an outlet;
- a first fluid flow pathway through the housing from the inlet to the outlet, the first fluid flow pathway having first means for resisting fluid flow therethrough;
- a second fluid flow pathway through the housing from the inlet to the outlet, the second fluid flow pathway having second means for resisting fluid flow therethrough;
- means actable by manual percutaneous pressure applied to the device when subcutaneously implanted, for selectively directing fluids through one of the first or the second fluid flow pathways, including means for occluding the second fluid flow pathway comprising plug means insertable into the second fluid flow pathway by manual percutaneous pressure applied to the housing, which plug means is retained in place to occlude the second fluid flow pathway; and
- siphon control device means situated adjacent to the outlet and forming a portion of the fluid flow pathways, for preventing fluid flow through the device in the presence of negative hydrostatic pressure at the outlet.

11. A fluid flow control device as set forth in claim 10, wherein the first means for resisting fluid flow comprises a first valve, the second means for resisting fluid flow comprises a second valve, and wherein the first fluid flow pathway directs fluid through the first and second valves, and the second fluid flow pathway bypasses the first valve and directs fluid through the second valve.

12. A fluid flow control device as set forth in claim 11, wherein the first and second valves each comprise a base including a valve passageway therethrough and a valve seat surrounding a portion of the valve passageway, and a flow control member attached to the base and contacting the valve seat in a manner normally occluding the valve passageway but selectively opening to permit controlled unidirectional flow therethrough.

13. A fluid flow control device as set forth in claim 12, wherein each flow control member includes a central support and a resilient membrane, the central support being attached to the respective base and extending therefrom to support the resilient membrane, the resilient membrane being generally arch-shaped and having a portion thereof capable of engaging the respective valve seat to occlude the respective valve passageway.

14. A fluid flow control device as set forth in claim 11, wherein the first valve provides a greater resistance to flow than the second valve.

15. A fluid flow control device as set forth in claim 11, including a pump providing means for flushing fluid from the fluid flow control device by application of percutaneous manual pressure to the device.

16. A fluid flow control device as set forth in claim 15, including means for temporarily occluding a portion of the fluid flow pathways adjacent to the inlet by application of percutaneous manual pressure to the housing such that actuation of the pump flushes fluid distally through the device.

17. A fluid flow control device as set forth in claim 15, including means for temporarily occluding a portion of the fluid flow pathways adjacent to the outlet by application of percutaneous manual pressure to the housing such that actuation of the pump flushes fluid proximally through the device.

18. A flow control device for use in a subsutaneously implanted physiological shunt system, comprising:
   a housing having an inlet and an outlet;
   a fluid flow path through the housing from the inlet to the outlet; and
   means for controlling fluid flow through the fluid flow path, the controlling means including means for permitting fluid flow through the fluid flow path when upstream fluid pressure exceeds downstream fluid pressure by a selected pressure differential, means for altering the selected pressure differential by manual percutaneous manipulation of the flow control device when subcutaneously implanted, a first normally closed valve which opens to permit fluid flow through the fluid flow path when upstream fluid pressure exceeds downstream fluid pressure by a first pressure differential, and a second normally closed valve which opens to permit fluid flow through the fluid flow path when upstream fluid pressure exceeds downstream fluid pressure by a second pressure differential, wherein the first pressure differential is greater than the second pressure differential;
   wherein the fluid flow path includes a first fluid conduit for directing fluid through the first normally closed valve, and a second fluid conduit which bypasses the first normally closed valve and directs fluid through the second normally closed valve; and
   wherein the means for altering the selected pressure differential includes means for altering the fluid flow path to bypass at least one of the valves, said altering means including a plug integrally formed with the housing and insertable into the second fluid conduit by manual percutaneous pressure applied to the device, which plug is retained in place to occlude the second fluid conduit in the absence of a dislodging percutaneous manipulation of the device.

19. A subcutaneously implantable shunt system, comprising:
   a shunt inlet;
   a shunt outlet;
   first valve means for controlling fluid flow from the shunt inlet to the shunt outlet;
   second valve means for controlling fluid flow from the shunt inlet to the shunt outlet;
   first fluid conduit means for directing fluid through the first and second valve means as the fluid passes through the shunt system;
   second fluid conduit means for bypassing the first valve means and directing fluid through the second valve means as the fluid passes through the shunt system; and
   means for selectively directing fluid through one of the first or second fluid conduit means.

20. A shunt system as set forth in claim 19, wherein the means for selectively directing fluid comprises means for occluding the second fluid conduit means.

21. A shunt system as set forth in claim 20, wherein the means for occluding the second fluid conduit means includes plug means insertable into the second fluid conduit means by manual percutaneous pressure applied to the shunt system when subcutaneously implanted.

22. A shunt system as set forth in claim 19, including a pump situated adjacent to the first valve means, wherein the pump provides means for flushing fluid through the shunt system by application of manual percutaneous pressure to the pump.

23. A shunt system as set forth in claim 19, including means for occluding a portion of the shunt system adjacent to the inlet by application of manual percutaneous pressure to the shunt system, and means for occluding a portion of the shunt system adjacent to the outlet by application of manual percutaneous pressure to the shunt system.

24. A shunt system as set forth in claim 19, including a siphon control device means situated between the second valve means and the outlet, for preventing fluid flow through the device in the presence of negative hydrostatic pressure at the outlet.

25. A shunt system as set forth in claim 19, wherein the first and second valve means each include a base having a fluid passageway therethrough and a valve seat surrounding a portion of the fluid passageway, and a flow control member attached to the base so that the flow control member contacts the valve seat in a manner normally occluding the fluid passageway but selectively opening to permit controlled unidirectional flow therethrough.

26. A shunt system as set forth in claim 25, wherein each flow control member includes a rigid nail-like central support and a resilient membrane, the central support being attached to the respective base and extending therefrom to support the resilient membrane, the resilient membrane being generally arch-shaped and having a portion thereof capable of engaging the respective valve seat to occlude the respective fluid passageway.

27. A flow control device having selectable alternative fluid pathways, for use in a subcutaneously implanted physiological shunt system, the flow control device comprising:
   a housing having an inlet and an outlet;
   means for occluding the inlet by application of percutaneous manual pressure to the device;
   a siphon control device adjacent to the outlet, which prevents fluid flow through the flow control device in the absence of positive upstream fluid pressure through the device or in response to negative hydrostatic downstream pressure on the device, the siphon control device providing means for occluding the outlet by application of percutaneous manual pressure to the device;
   a flushing reservoir adjacent to the inlet having overlying resiliently deformable dome forming a portion of the housing, the flushing reservoir providing means for flushing fluid through the flow control device by application of percutaneous manual pressure to the device to depress the dome;
   a first valve situated between the flushing reservoir and the siphon control device, for controlling fluid flow from the inlet to the outlet;
   a second valve situated between the first valve and the siphon control device, for controlling fluid flow from the inlet to the outlet;

first fluid conduit means for directing fluid through the first and second valves as the fluid passes through the flow control device;

second fluid conduit means for bypassing the first valve and directing fluid through the second valve as the fluid passes through the flow control device; and means for selectively directing fluid through one of the first or second fluid conduit means, the means for selectively directing fluid including means for occluding the second fluid conduit means.

28. A flow control device as set forth in claim 27, wherein the first and second valves each include a base having a valve passageway therethrough and a valve seat surrounding a portion of the valve passageway, and a flow control member attached to the base and contacting the valve seat in a manner normally occluding the valve passageway but selectively opening to permit controlled unidirectional flow therethrough.

29. A flow control device as set forth in claim 27, wherein the means for occluding the second fluid conduit means includes plug means integrally formed with the housing and insertable into the second fluid conduit means by manual percutaneous pressure applied to the device, which plug means is retained in place to occlude the second fluid conduit means until displaced therefrom by the selective application of manual percutaneous pressure to the device.

30. A fluid flow control device, comprising:
an inlet;
an outlet;
a fluid flow pathway between the inlet and the outlet;
a siphon control device situated adjacent to the outlet and forming a portion of the fluid flow pathway;
at least two valves for restricting the flow of fluid through the device, the valves being situated serially within the fluid flow pathway between the inlet and the siphon control device; and
means for altering the fluid flow pathway to selectively bypass at least one of the valves;
wherein the fluid flow pathway includes first fluid conduit means for directing fluid through all of the at least two valves, and a second fluid flow conduit means for directing the fluid to bypass at least one of the valves; and
wherein the means for altering the fluid flow pathway includes means for occluding the second fluid flow conduit means, the occluding means comprising plug means insertable into the second fluid flow conduit means by manual percutaneous pressure applied to the device, which plug means is retained in place to occlude the second fluid flow conduit means in the absence of a dislodging percutaneous manipulation of the device.

31. A fluid flow control device, comprising:
a housing having an inlet and an outlet;
a first fluid flow pathway through the housing from the inlet to the outlet, the first fluid flow pathway having a first valve for resisting fluid flow therethrough;
a second fluid flow pathway through the housing from the inlet to the outlet, the second fluid flow pathway having a second valve for resisting fluid flow therethrough; and
means actuable by manual percutaneous pressure applied to the device when subcutaneously implanted, for selectively directing fluids through one of the first or the second fluid flow pathways, wherein the first fluid flow pathway directs fluid through the first and second valves, and the second fluid flow pathway bypasses the first valve and directs fluid through the second valve.

32. A fluid flow control device as set forth in claim 31, including a pump between the inlet and the first valve, wherein the pump provides means for flushing fluid from the fluid flow control device by application of percutaneous manual pressure to the device.

33. A fluid flow control device as set forth in claim 32, including means for temporarily occluding a portion of the fluid flow pathways adjacent to the inlet by application of percutaneous manual pressure to the housing such that actuation of the pump flushes fluid distally through the device.

34. A fluid flow control device as set forth in claim 32, including means for temporarily occluding a portion of the fluid flow pathways adjacent to the outlet by application of percutaneous manual pressure to the housing such that actuation of the pump flushes fluid proximally through the device.

* * * * *

UNITED STATES PATENT AND TRADEMARK OFFICE
CERTIFICATE OF CORRECTION

PATENT NO. : 5,154,693

DATED : October 13, 1992

INVENTOR(S) : Gary P. East, David A. Watson

It is certified that error appears in the above-identified patent and that said Letters Patent is hereby corrected as shown below:

In column 7, line 33, delete "tee" and insert therefor --the--.

In column 11, line 64, delete "f" and insert therefor --of--.

In column 14, line 57, after the word "having" insert --an--.

Signed and Sealed this

Twenty-first Day of September, 1993

Attest:

BRUCE LEHMAN

Attesting Officer

Commissioner of Patents and Trademarks